(12) United States Patent
Just

(10) Patent No.: US 7,442,179 B1
(45) Date of Patent: Oct. 28, 2008

(54) PRE-FILL APPLICATOR

(76) Inventor: Troy M. Just, 7524 Brummond Dr., Lincoln, NE (US) 68516

( * ) Notice: Subject to any disclaimer, the term of this patent is extended or adjusted under 35 U.S.C. 154(b) by 1180 days.

(21) Appl. No.: 10/668,785

(22) Filed: Sep. 23, 2003

(51) Int. Cl.
*A61F 6/06* (2006.01)
*A61F 13/02* (2006.01)
*A61F 13/15* (2006.01)
*A61F 13/20* (2006.01)
*A61M 31/00* (2006.01)

(52) U.S. Cl. .............................. 604/18; 604/11; 604/15; 604/16; 604/60; 604/385.18; 424/430; 424/431

(58) Field of Classification Search ......... 604/181–186, 604/904
See application file for complete search history.

(56) References Cited

U.S. PATENT DOCUMENTS 6,280,418 B1 * 8/2001 Reinhard et al. ............ 604/187
6,364,854 B1 * 4/2002 Ferrer et al. .................. 604/60

* cited by examiner

*Primary Examiner*—Tatyana Zalukaeva
*Assistant Examiner*—Melanie J Hand
(74) *Attorney, Agent, or Firm*—Thomte Patent Law Office; Dennis L. Thomte

(57) ABSTRACT

A pre-fill vaginal applicator comprising a tubular barrel having an open end and a dispensing end provided with at least one dispensing opening formed therein. A selectively removable closure, such as a snap cap or threaded cap, closes the dispensing end of the barrel. A resilient piston is selectively slidably positioned in the barrel and has an outer surface which is in sealing contact with the inner surface of the barrel to define a medication reservoir between the piston and dispensing end of the barrel. An elongated plunger is adapted to be inserted into the open end of the barrel so that the inner end thereof may be detachably connected to the piston. After the plunger has been connected to the piston, inward movement of the plunger causes the piston to force medication from the medication reservoir outwardly through the dispensing opening. Outward movement of the plunger with respect to the piston causes the plunger to disconnect from the piston.

6 Claims, 8 Drawing Sheets

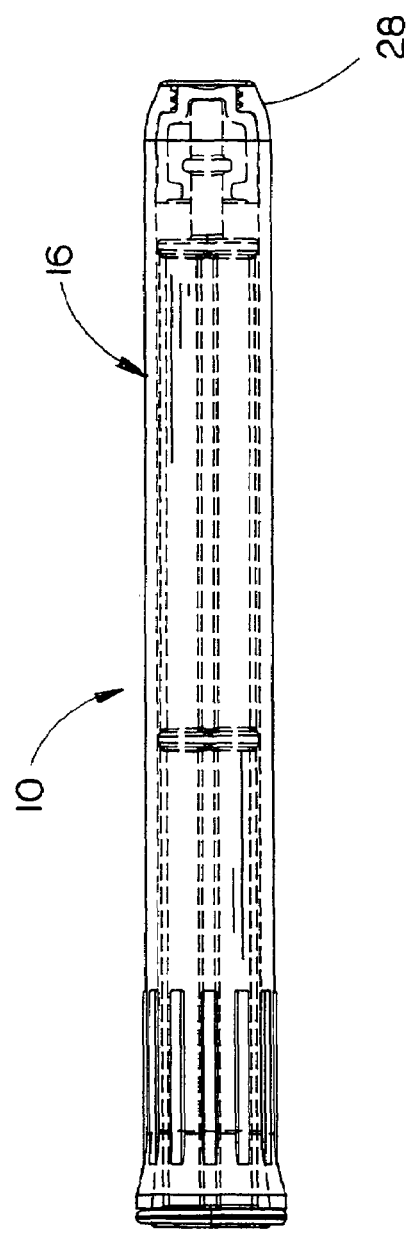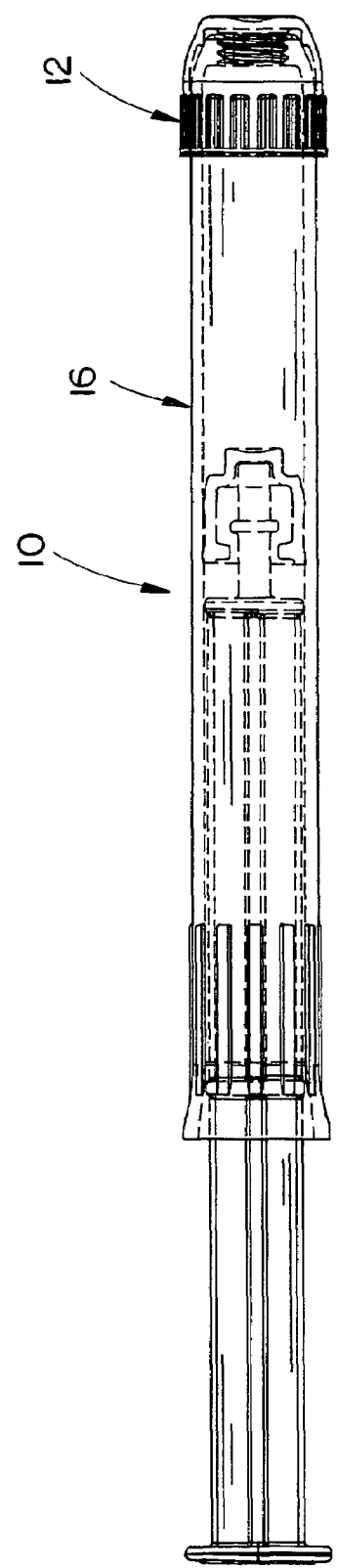
FIG. 1
FIG. 2

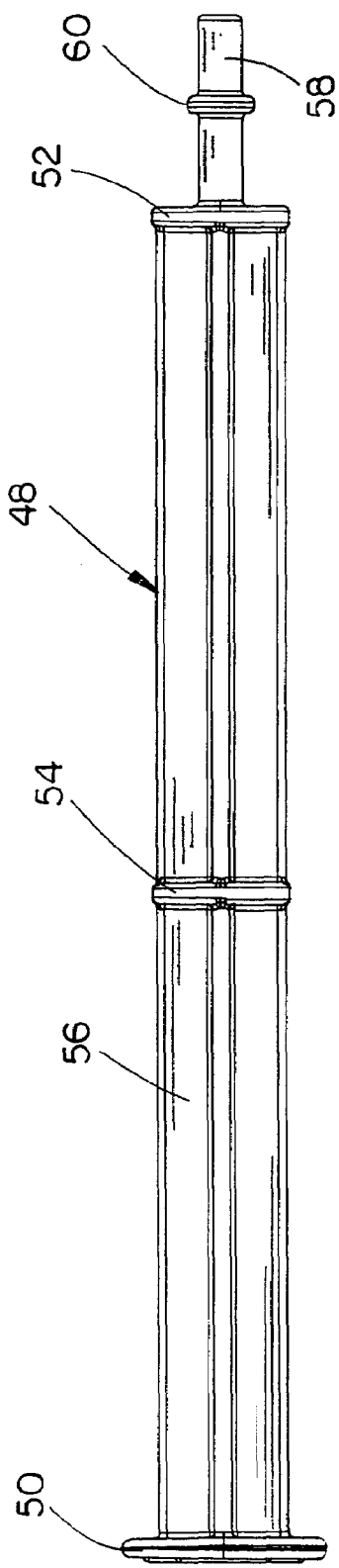
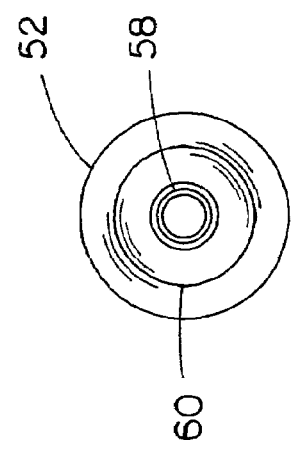
FIG. 8
FIG. 6
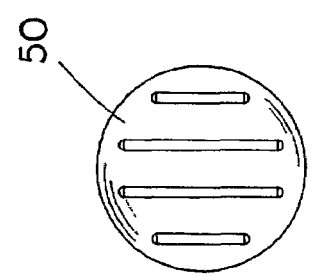
FIG. 7

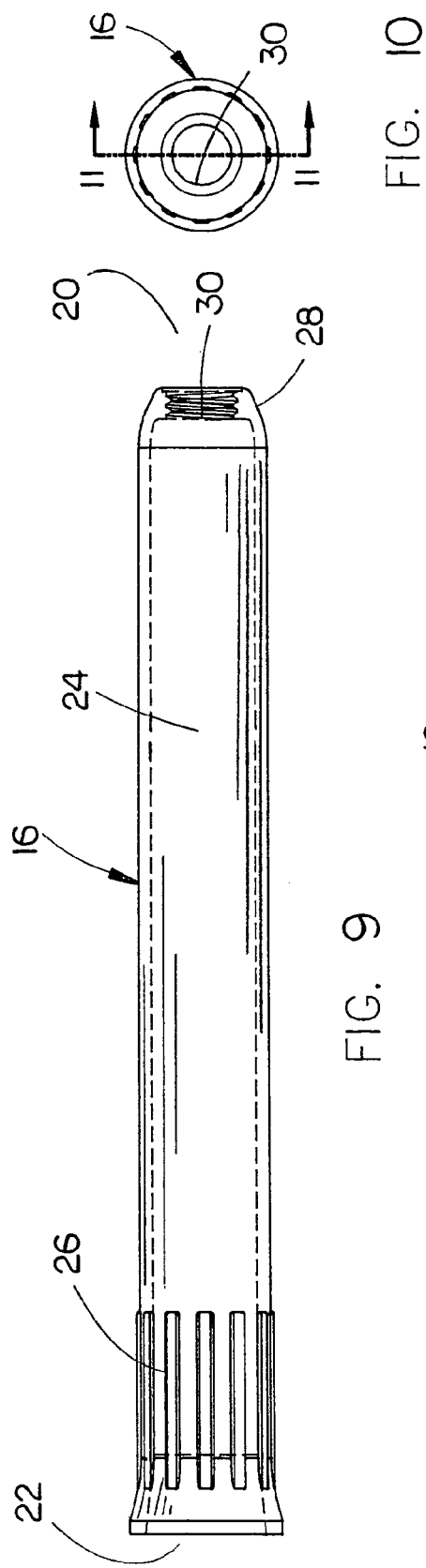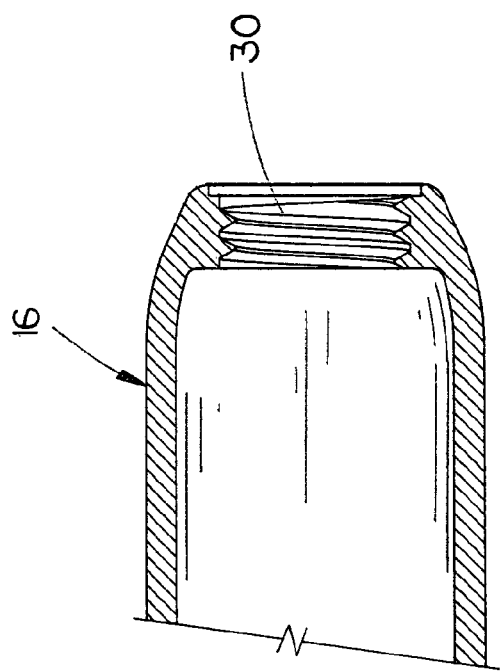

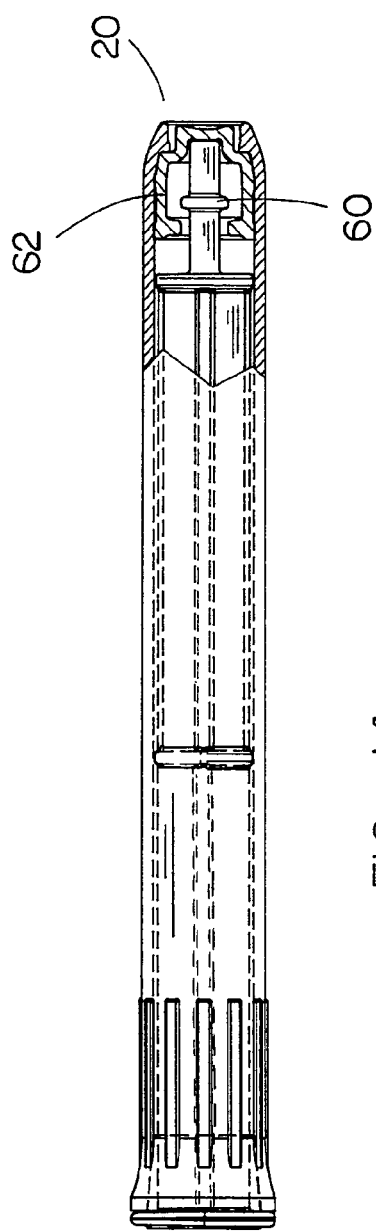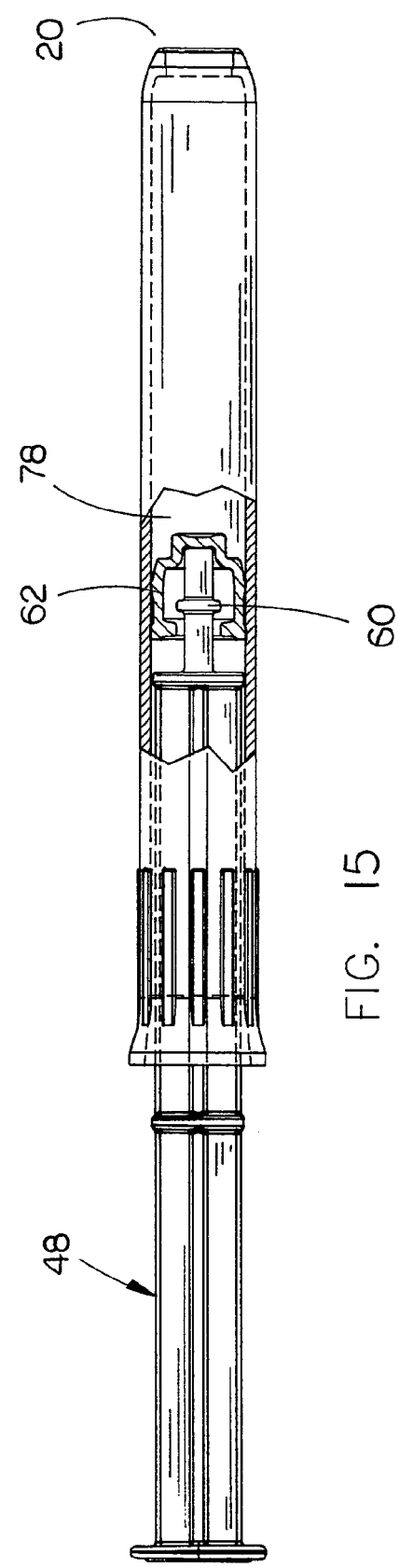

PRE-FILL APPLICATOR

BACKGROUND OF THE INVENTION

1. Field of the Invention

This invention relates to a pre-fill applicator and more particularly to a pre-fill vaginal applicator. Further, the invention relates to a vaginal applicator which is designed to discourage the re-use of the same.

2. Description of the Related Art

The use of vaginal applicators for application of medication is well known in the art. Although the prior art vaginal applicators have met with success, the same suffer from certain drawbacks or disadvantages. Many of the prior art vaginal applicators are extremely complicated thereby making the manufacture of the same a difficult task. Additionally, certain of the prior art vaginal applicators have a blunt dispensing tip which makes the use thereof uncomfortable to the person using the same. Further, the prior art vaginal applicators are designed in such a way that they may possibly be re-used which may lead to the spread of disease. The prior art vaginal applicators, when pre-filled with medication, do not have adequate sealing of the medication reservoir which results in some evaporation of the medication during shipment and storage. Lastly, the prior art vaginal applicators normally do not have a means for ensuring that substantially all of the medication is dispensed from the applicator.

SUMMARY OF THE INVENTION

The pre-filled vaginal applicator of this invention comprises a tubular barrel having an open end and a dispensing end provided with at least one opening formed therein. A selectively removable closure, such as a snap cap or threaded cap, closes the dispensing end of the barrel. A resilient piston having first and second ends is selectively slidably positioned in the barrel and has an outer surface which is in sealing contact with the inner surface of the barrel to define a medication reservoir between the first end of the piston and the dispensing end of the barrel. The piston, prior to insertion into the barrel, has a larger outside diameter than the inside diameter of the barrel so that the piston is in a compressed state against the inner surface of the barrel when the piston is inserted into the barrel. The second end of the piston has an opening extending thereinto which terminates between the first and second ends of the piston. An elongated plunger having first and second ends is adapted to be inserted into the open end of the barrel so that the first end thereof may be inserted into the opening in the second end of the piston to detachably connect the plunger to the piston. The plunger, when connected to the piston and being moved towards the dispensing end of the barrel, causes the resilient piston to longitudinally stretch to permit the piston to slide towards the dispensing end of the barrel, thereby forcing medication in the medication reservoir to be ejected from the opening in the dispensing end of the barrel. The first end of the plunger is detachably connected to the piston in such a manner so that movement of the plunger away from the piston will cause the first end of the plunger to disconnect from the piston. The piston is constructed of a material so as to destruct if an attempt is made to manually move the piston towards the open end of the barrel by applying force against the first end thereof, thereby ensuring that the applicator may not be re-used.

It is therefore a principal object of the invention to provide an improved pre-fill applicator.

A further object of the invention is to provide an improved pre-fill vaginal applicator.

Yet another object of the invention is to provide a vaginal applicator which is designed so as to be comfortable to the person utilizing the same.

Still another object of the invention is to provide a vaginal applicator comprised of four pieces, that is, a barrel, plunger, piston and cap.

Still another object of the invention is to provide a vaginal applicator including a threaded cap which is designed to be threadably mounted on the dispensing end of the barrel in such a manner so that the threads do not come into contact with the patient's vagina when the cap has been removed from the barrel and the applicator is inserted into the patient's vagina.

Still another object of the invention is to provide a pre-fill vaginal applicator which is designed so as to prevent its re-use.

Still another object of the invention is to provide a pre-fill vaginal applicator of the type described which reduces evaporation of the medication in the medication reservoir during shipment or storage.

Yet another object of the invention is to provide an applicator of the type described which is economical of manufacture, durable in use and refined in appearance.

These and other objects will be apparent to those skilled in the art.

BRIEF DESCRIPTION OF THE DRAWINGS

FIG. 1 is a side elevational view of the vaginal applicator of this invention with the plunger thereof in its fully extended or dispensing condition;

FIG. 2 is a view similar to FIG. 1 except that the piston is in its original pre-fill position;

FIG. 6 is a side view of the plunger of this invention;

FIG. 7 is an end view of the plunger of FIG. 6 as seen from the left side of FIG. 6;

FIG. 8 is an end view of the plunger of FIG. 6 as seen from the right side of FIG. 6;

FIG. 9 is an elevational view of the barrel portion of the applicator;

FIG. 10 is an end view of the barrel of FIG. 9 as seen from the right side of FIG. 9;

FIG. 11 is a partial enlarged sectional view as seen on lines 11-11 of FIG. 10;

FIG. 14 is a side elevational view of a modified form of the applicator of with portions thereof cut away to more fully illustrate the invention;

FIG. 15 is a side elevational view of the applicator of FIG. 14 with portions thereof cut away to more fully illustrate the invention;

DESCRIPTION OF THE PREFERRED EMBODIMENT

Figure 3:
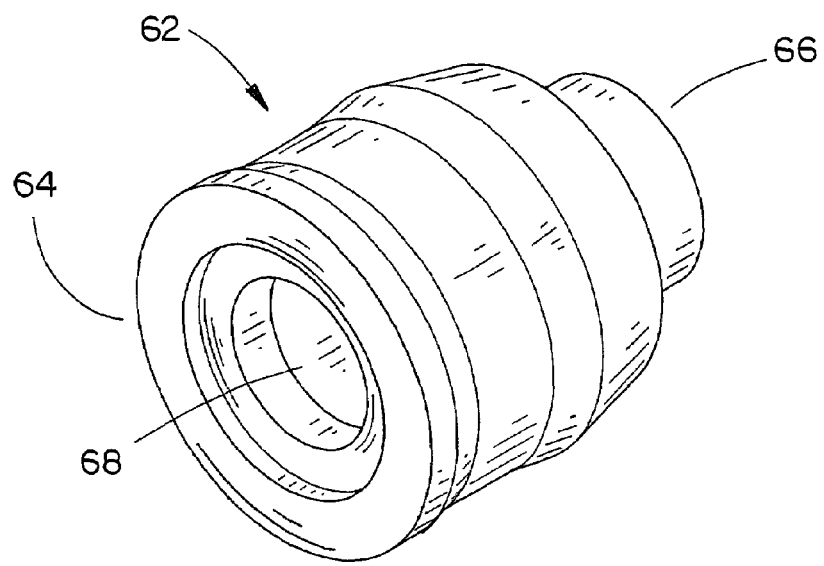
FIG. 3 is a rear perspective view of the piston of this invention.

The numeral 10 refers generally to the pre-fill vaginal applicator of this invention. The dispensing end of the barrel of the applicator may be either closed by a threaded cap 12 or by a snap-fit cap 14. The dispensing end of the barrel is designed somewhat differently depending upon the threaded cap 12 or the snap cap 14 is being utilized, as will be described hereinafter. The numeral 16 refers to the barrel which is adapted to receive the threaded cap 12 while the numeral 18 refers to the barrel which is designed to receive the snap cap 14.

Barrel 16 includes a dispensing end 20 and an open end 22. Barrel 16 is provided with a bore 24 extending between the ends 20 and 22. As seen in FIG. 9, the open end 22 of the barrel 16 is slightly enlarged for handling purposes and has a plurality of ribs 26 protruding from the outside surface thereof to enable the person using the same to conveniently grasp the barrel. Barrel 16 is provided with a tapered portion 28 at its dispensing end for comfort purposes. An internally threaded dispensing opening 30 is provided at the dispensing end 20, as seen in FIGS. 9 and 11.

Figure 13:
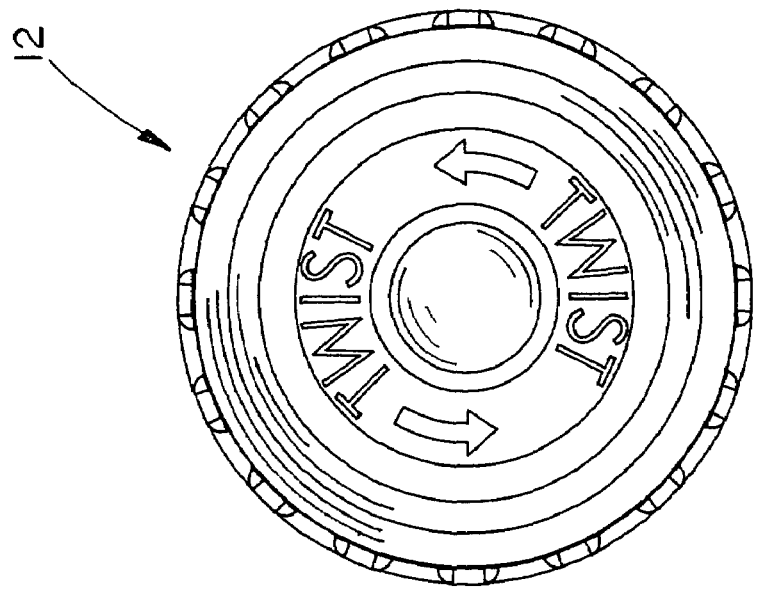
FIG. 13 is an end view of the cap of FIG. 12 as seen from the right side of FIG. 12.
Figure 12:
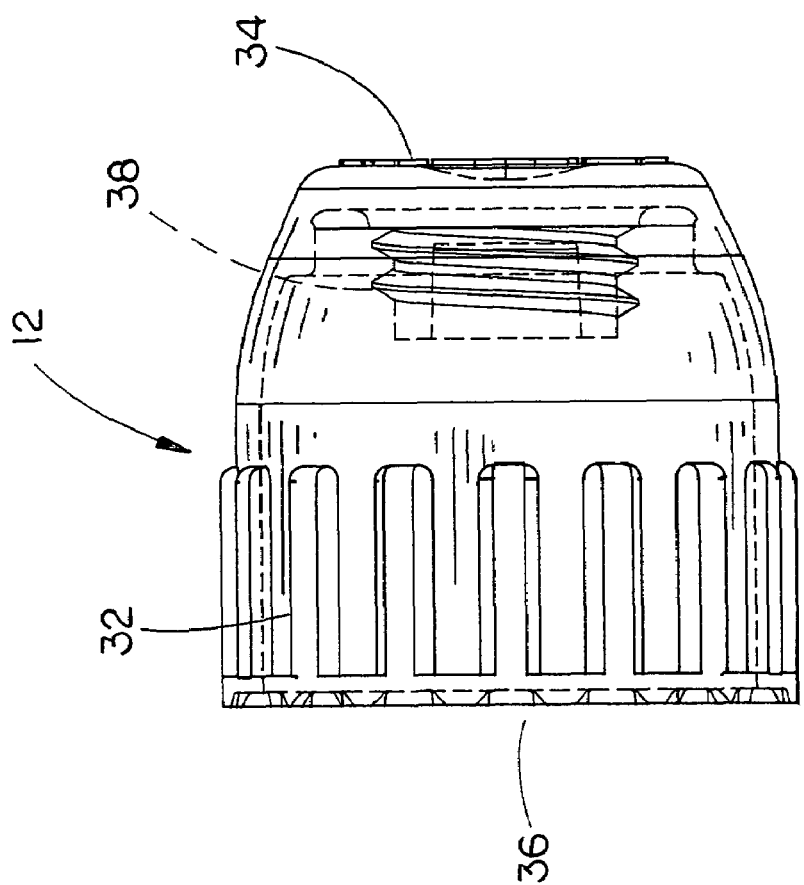
FIG. 12 is a side elevational view of a threaded cap closure which is used with the barrel of FIGS. 9-11.
Figure 17:
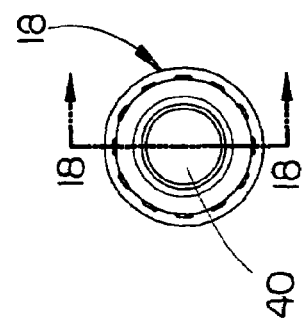
FIG. 17 is an end view of the barrel of FIG. 16 as seen from the right side of FIG. 16.
Figure 16:
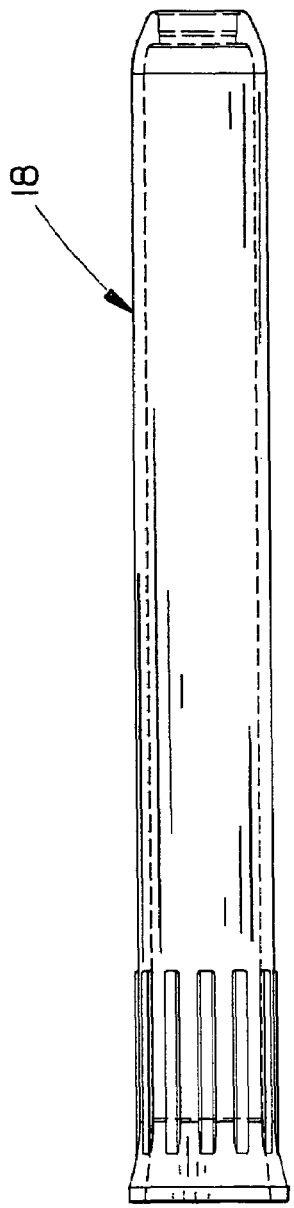
FIG. 16 is a side elevational view of the barrel of FIG. 14 which is designed to have a snap-fit cap mounted thereon.

Cap 12 is illustrated in FIGS. 12 and 13 and is provided with a plurality of spaced-apart ridges or ribs 32 at its outer surface to enable the person using the same to conveniently grip the cap to unscrew the same from the barrel 16. Cap 12 includes a closed outer end 34 upon which the words "TWIST" and arrow legends are provided for purposes of direction. Cap 12 has a compartment or cavity 36 extending into the inner end thereof and which terminates short of the sealed end 34. An externally threaded stud portion 38 is provided is in compartment or cavity 36 and is adapted to be threadably received by the internally threaded opening 30 in barrel 16 to secure the cap 12 onto the dispensing end of the barrel 16. When cap 12 is secured to the barrel 16 as described above, the dispensing end of the barrel 16 is sealed.

Figure 18:
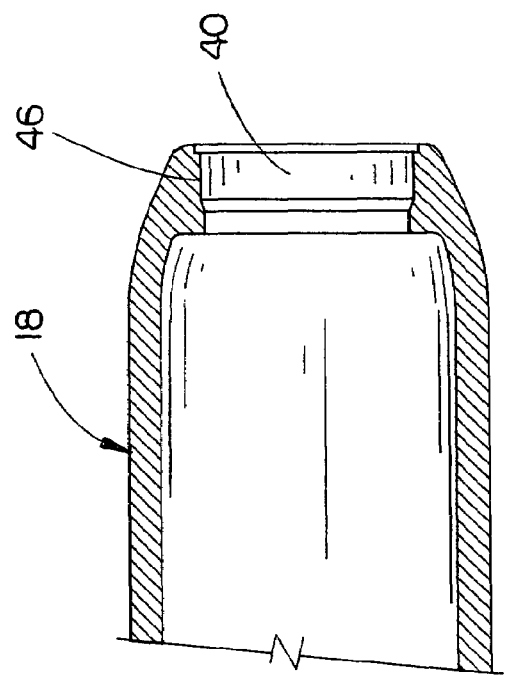
FIG. 18 is a partial enlarged sectional view as seen on lines 18-18 of FIG. 17.
Figure 20:
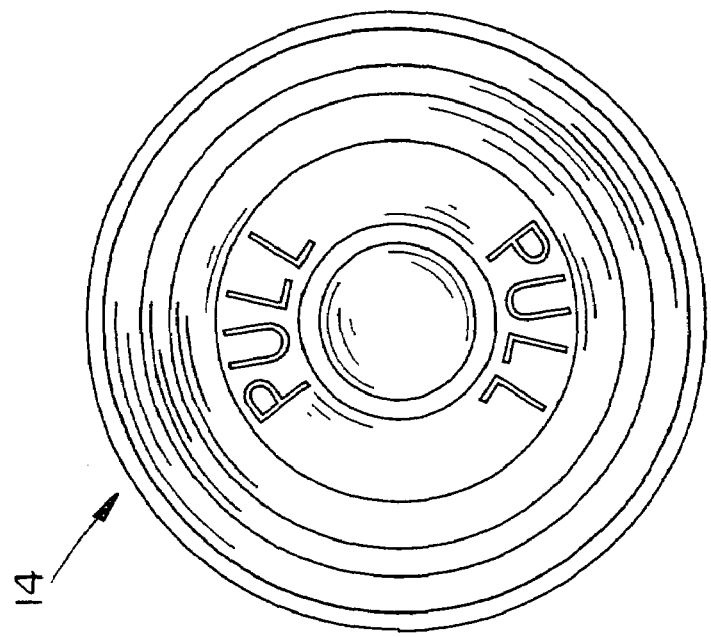
FIG. 20 is an end view of the closure of FIG. 19 as seen from the right side thereof.
Figure 19:
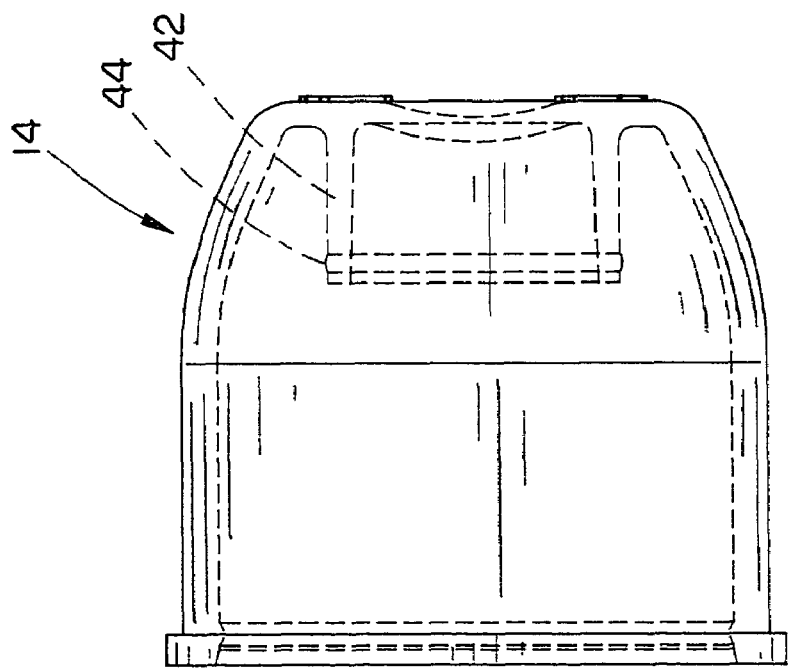
FIG. 19 is a side elevational view of a snap-fit cap for use on the barrel of FIG. 16.

Barrel 18 is identical to barrel 16 except that the dispensing end of the barrel 18 does not have the internally threaded opening 30 at its dispensing end but has an opening 40, as best seen in FIG. 18. Cap 14, as seen in FIG. 19, has a stud portion 42 which has an annular rib 44 provided thereon. When cap 14 is mounted on barrel 18 to close the dispensing end thereof, stud portion 42 is received by the opening 40 with the rib 44 frictionally engaging the wall surface 46 which extends around opening 40 to assist in sealably maintaining the cap 14 on the barrel 18. As seen in FIG. 2, the closed end of cap 14 has the words "PULL" provided thereon for purposes of direction.

The plunger utilized in both barrels 16 and 18 is referred to generally by the reference numeral 48. Plunger 48 is provided with a disc-shaped end portion 50 at its outer end and a disc-shaped portion 52 which is spaced from the inner end of the plunger. A disc-shaped portion 54 is also provided on the plunger 48, as seen in FIG. 6. Four spaced-apart wall portions 56 extend between the disc portions 50, 54 and 52. End portion 58 extends from disc portion 52 and has an annular, enlarged rib 60 provided thereon, as seen in FIG. 6. The length of the end portion 58 is slightly longer than the length of the piston 62 to permit the piston 62 to longitudinally stretch as the plunger 48 slidably moves the piston 62 inwardly within the barrels 16 and 18.

Figures 4, 5:
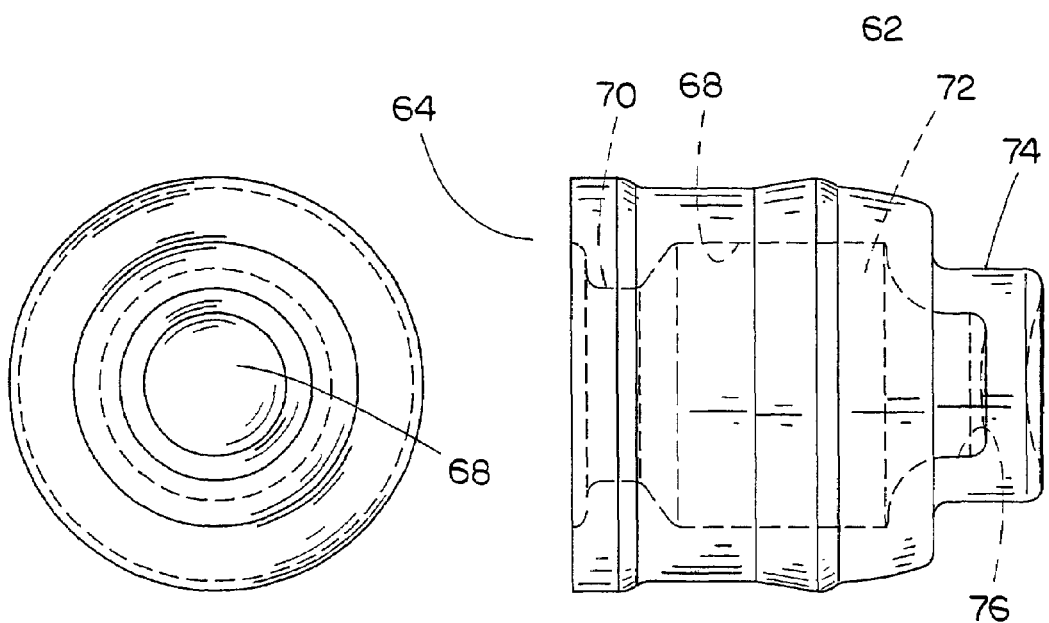
FIG. 4 is an end elevational view of the piston as seen from the left side of FIG. 3.
FIG. 5 is a side elevational view of the piston of FIG. 3.

Piston 62 has ends 64 and 66 with an opening 68 extending into end 64, as seen in FIGS. 3 and 5. Opening 68 defines a throat portion 70 which is positioned between end 64 and the central compartment or cavity 72. As seen in FIG. 5, piston 62 includes a reduced diameter portion 74 having an internal cavity 76 provided therein. The reduced diameter portion 74 is designed such that it will be received by the threaded opening 30 in barrel 16 or the opening 40 in barrel 18 as will be described in more detail hereinafter.

The applicator of this invention is comprised of four pieces or components, that is, a barrel 16 or 18, cap 12 or 14, piston 62 and plunger 48. Preferably, the barrels 16 and 18, the plunger 48 and the caps 12, 14 are fabricated from Fortiflex® T50-2000 available from Solvay Polymers, Inc., 3333 Richmond Avenue, Houston, Tex. 77098. Fortiflex® T50-2000 is a high density, narrow molecular weight polyethylene copolymer intended for applications requiring a glossy surface finish and reasonably good impact strength and rigidity. It is characterized by a high melt index which allows easy processing of medium to thin-walled articles. Preferably, the piston 62 is fabricated from Santoprene® 8000 Rubber 8281-55 available from Advanced Elastomer Systems, L.P., 388 South Main Street, Akron, Ohio 44311-1059. Santoprene® 8000 Rubber 8281-55 is a colorable thermoplastic medical grade elastomer. After the parts have been fabricated, the piston 62 is inserted into the compartment 24 of either the barrel 16 or 18 at a predetermined location therein so that a medication reservoir 78 of predetermined size is defined between the inner end of the piston 62 and the dispensing end 20 of the barrel. The positioning of the piston 62 within the barrel 16 or 18 will be determined by the amount of medication to be subsequently introduced into the medication reservoir. The barrel with the piston therein, the cap and the plunger are then shipped to the location where medication will be introduced into the medication reservoir either through threaded opening 30 in barrel 16 or the opening 40 in barrel 18. After the medication has been introduced into the reservoir 78, the dispensing end of the barrel will be closed by either the caps 12 or 14. The piston 62 seals one end of the medication reservoir 78 while the caps 12 or 14 seal the other end of the reservoir 78, thereby preventing evaporation of the medication prior to it being used. The capped barrel 16 or 18 having the piston 62 therein and the medication in the reservoir 78 is then placed in a package together with a plunger 48 for shipment to the pharmacy.

When it is desired to dispense the medication, the components are removed from their sealed package and the plunger 48 is then inserted into the open end of the barrel until the inner end of the end portion 58 is received by and engages the piston, as illustrated in FIG. 15. The diameter of the piston 62, prior to being installed in the barrel, is greater than the inside diameter of the compartment or cavity 24 of the barrel so ensure that the piston will properly seal against the inner surface of the cavity 24. The compression of the piston 62 as it is placed in the barrel causes the throat portion 70 to be narrowed so that the rib 60 may be snap-fitted into the compartment 68, as seen in FIG. 15.

The cap is then removed from the barrel and the barrel is inserted into the vagina with the curved or tapered inner end of the barrel making the insertion thereof more comfortable than if the inner end of the barrel were blunt. Once the applicator has been properly positioned within the vagina, the plunger 48 is then moved inwardly with respect to the barrel which causes the piston 62 to longitudinally stretch to enhance the sliding movement of the piston 62 with respect to the barrel. The piston 62 will normally stretch until its end 64 engages the disc-shaped member 52. The plunger 48 is moved inwardly with respect to the barrel until the end portion 74 of the piston 62 is received within either the threaded opening 30 in the barrel 16 or the opening 40 in barrel 18. The movement of the end portion 74 into either the threaded opening 30 or the opening 40 causes all of the medication within the reservoir to be dispensed therefrom without wastage of medication.

When the medication has been completely dispensed from the applicator, the applicator is removed from the vagina. The piston will not be moved from its fully extended dispensing position of FIG. 14 should the plunger 48 be pulled outwardly from the barrel since the rib 60 will pass outwardly through the throat 70 causing a disconnection of the plunger 48 from the piston 62. This discourages re-use of the applicator. If a person should introduce a long object into the dispensing end of the barrel in an effort to push the piston 62 outwardly through the open end of the barrel, the frangible construction of the piston 62 will cause the piston to destruct upon pressure being applied to end portion 74. In other words, the object which is being used to force the piston outwardly from the barrel will pierce through the end portion 74 of the piston, thereby preventing re-use of the piston.

Thus it can be seen that the invention accomplishes at least all of its stated objectives.

I claim:

1. A pre-fill vaginal applicator, comprising:
    a tubular barrel having a dispensing end provided with at least one opening formed therein and an open end;
    said barrel having an inner surface;
    a selectively removable closure closing said dispensing end of said barrel;
    a resilient piston having first and second ends, selectively slidably positioned in said barrel;
    said piston having an outer surface which is in sealing contact with said inner surface of said barrel to define a medication reservoir between said first end of said piston and said dispensing end of said barrel;
    said second end of said piston having an opening extending thereinto which terminates between said first and second ends of said piston;
    an elongated plunger having first and second ends adapted to be inserted into said open end of said barrel whereby said first end thereof may be inserted into said opening in said second end of said piston to detachably connect said plunger to said piston;
    said piston, prior to insertion into said barrel, having a larger outside diameter than the inside diameter of said barrel whereby said piston is in a compressed state against said inner surface of said barrel when said piston is inserted into said barrel;
    said plunger, when connected to said piston and being moved towards said dispensing end of said barrel, causing said resilient piston to longitudinally stretch to permit said piston to slide towards said dispensing end thereby forcing medication in said medication reservoir to be ejected from said opening in said dispensing end of said barrel;
    said first end of said plunger being detachably connected to said piston whereby movement of said plunger away from said piston will cause said first end of said plunger to disconnect from said piston so that said piston remains in said barrel thereby ensuring that the applicator may not be reused.

2. The applicator of claim 1 wherein said first end of said piston has a portion thereof shaped so as to be receivable within said opening formed in said dispensing end of said barrel.

3. The applicator of claim 1 wherein said piston is constructed so as to destruct if an attempt is made to manually move said piston towards said open end of said barrel by applying force against said first end thereof, thereby further ensuring that the applicator may not be reused.

4. A vaginal applicator, comprising:
    a tubular barrel having a dispensing end provided with at least one opening formed therein and an open end;
    said barrel having an inner surface;
    a resilient piston having first and second ends, selectively slidably positioned in said barrel;
    said piston having an outer surface which is in slidable sealing contact with said inner surface of said barrel to define a medication reservoir between said first end of said piston and said dispensing end of said barrel;
    said second end of said piston having an opening extending thereinto which terminates between said first and second ends of said piston;
    an elongated plunger having first and second ends adapted to be inserted into said open end of said barrel whereby said first end of said plunger may be inserted into said opening in said second end of said piston to detachably connect said plunger to said piston;
    said piston, prior to insertion into said barrel, having a larger outside diameter than the inside diameter of said barrel whereby said piston is in a compressed state against said inner surface of said barrel when said piston is inserted into said barrel;
    said plunger, when connected to said piston and being moved towards said dispensing end of said barrel, causing said resilient piston to longitudinally stretch to permit said piston to slide towards said dispensing end thereby forcing medication in said medication reservoir to be ejected from said opening in said dispensing end of said barrel;
    said first end of said plunger being detachably connected to said piston whereby movement of said Plunger away from said piston will cause said first end of said plunger to disconnect from said piston so that said piston remains in said barrel thereby ensuring that the applicator may not be reused.

5. The applicator of claim 4 wherein said first end of said piston has a portion thereof shaped so as to be receivable within said opening formed in said dispensing end of said barrel.

6. The applicator of claim 4 wherein said piston is constructed so as to destruct if an attempt is made to manually move said piston towards said open end of said barrel by applying force against said first end thereof, thereby ensuring that the applicator may not be reused.

* * * * *